(12) United States Patent
KenKnight et al.

(10) Patent No.: US 7,996,074 B2
(45) Date of Patent: Aug. 9, 2011

(54) SYSTEM AND METHOD FOR PROVIDING CLOSELY-FOLLOWED CARDIAC THERAPY MANAGEMENT THROUGH AUTOMATED PATIENT CARE

(75) Inventors: Bruce H. KenKnight, Maple Grove, MN (US); Yatheendhar D. Manicka, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1124 days.

(21) Appl. No.: 11/378,677

(22) Filed: Mar. 17, 2006

(65) Prior Publication Data

US 2007/0219419 A1    Sep. 20, 2007

(51) Int. Cl.
*A61B 5/04* (2006.01)
(52) U.S. Cl. ............ 600/513; 600/508; 600/509; 607/9; 607/30; 607/32
(58) Field of Classification Search .................. 600/508, 600/509, 513, 516, 517, 518; 607/30, 32, 607/9; 340/573.1
See application file for complete search history.

(56) References Cited

U.S. PATENT DOCUMENTS

| | | | |
|---|---|---|---|
| 6,024,699 A | 2/2000 | Surwit et al. | |
| 6,083,248 A | 7/2000 | Thompson | |
| 6,168,563 B1 | 1/2001 | Brown | |
| 6,171,256 B1 | 1/2001 | Joo et al. | |
| 6,263,245 B1 | 7/2001 | Snell | |
| 6,416,471 B1 | 7/2002 | Kumar et al. | |
| 6,418,346 B1 | 7/2002 | Nelson et al. | |
| 6,480,733 B1 * | 11/2002 | Turcott | 600/516 |
| 6,804,558 B2 * | 10/2004 | Haller et al. | 607/30 |
| 6,827,670 B1 | 12/2004 | Stark et al. | |
| 7,027,872 B2 | 4/2006 | Thompson | |
| 2005/0231374 A1 * | 10/2005 | Diem et al. | 340/573.1 |

OTHER PUBLICATIONS

Health Insurance Portability And Accountability Act of 1996, Pub. L. No. 104-191, 110 Stat. 1936 (1996).
E. Hammond, "National Committee On Vital And Health Statistics, Subcommittee On Health Data Needs, Standards And Security," http://www.ncvhs.hhs.gov/970211t3.htm, pp. 1-4 (Feb. 11, 1997).
Security And Electronics Signature Standards, 63 Fed. Reg. 155 (proposed Aug. 12, 1998).
W. Diffie, "The First Ten Years Of Public-Key Cryptography," Proceedings of the IEEE, vol. 76, No. 5, pp. 560-577 (May 1988).
E. Braunwald, ed., "Heart Disease—A Textbook of Cardiovascular Medicine," Ch. 17, pp. 492-514, W.B. Saunders Co. ($5^{th}$ ed. 1997).

* cited by examiner

*Primary Examiner* — Carl H Layno
*Assistant Examiner* — Pamela M Bays
(74) *Attorney, Agent, or Firm* — Pauly, Devries Smith & Deffner, L.L.C.

(57) ABSTRACT

A system and method for providing closely-followed cardiac therapy management through automated patient care is presented. A patient under remote care is enrolled in a monitoring program following commencement of a cardiac therapy regimen to be undertaken by the patient. A wearable monitor, including one or more patient physiology sensors and a wireless interface providing enabling bi-directional data exchange, is provided to the patient. Patient physiometry, including quantitative physiological measures, is periodically collected from the wearable monitor over the wireless interface concomitant to performance of the cardiac therapy regimen. The patient physiometry is evaluated to determine a trend indicating an onset, progression, regression, absence of, and status quo of patient health status.

10 Claims, 6 Drawing Sheets

SYSTEM AND METHOD FOR PROVIDING CLOSELY-FOLLOWED CARDIAC THERAPY MANAGEMENT THROUGH AUTOMATED PATIENT CARE

FIELD OF THE INVENTION

The invention relates in general to automated patient management and, specifically, to a system and method for providing closely followed cardiac therapy management through automated patient care.

BACKGROUND OF THE INVENTION

Cardiac therapy can play a major role in improving the well being of cardiovascular patients. The therapy prescribed can depend upon the clinical stage of the cardiovascular disorder and can include a combination of medication, dietary restriction or modification, and physical activity limits. Other therapies are possible. Therapy can continue indefinitely as an aid to preventing disease progression and improving clinical status, as well as to reduce future risk.

Generally, patients that undergo a managed therapy regimen following a diagnosis and treatment for a cardiovascular disorder, such as coronary artery bypass grafting or percutaneous coronary artery stenting, benefit from improved survival rate and decreased co-morbidity occurrence. Effective cardiac therapy can help improve quality and length of life and can be instrumental in preventing the progress of the underlying cardiovascular syndrome, provided the patient conscientiously adheres to the regimen.

The management of cardiovascular disorders generally includes three aspects, such as described in E. Braunwald, ed., "Heart Disease—A Textbook of Cardiovascular Medicine," Ch. 17, pp. 492-514, W.B. Saunders Co. (5$^{th}$ ed. 1997), the disclosure of which is incorporated by reference. The first aspect, removing or ameliorating the underlying cause, addresses evaluating treatable causes through, for instance, surgical intervention to correct or repair cardiac abnormalities. The second aspect, removing precipitating causes, includes recognizing, treating, and preventing specific entities that cause or exacerbate the cardiac condition. Precipitating causes include arrhythmias, systemic infection, pulmonary embolism, physical, environmental and emotional excesses, cardiac infection and inflammation, unrelated co-morbidities, cardiac depressants or salt-retaining drugs, high-output states, and development of a second form of heart disease. The third aspect addresses controlling the cardiac disorder state.

Detection and diagnosis of significant changes in health status can remain undetected in non-closely followed cardiac patients. Even patients with serious underlying cardiac conditions may be relatively asymptomatic provided that they carefully adhere to the treatment regimen. Departures from a treatment regimen are common precipitating causes and can lead to patient decompensation. For instance, stented patients are at risk of developing atrial fibrillation, ventricular tachycardical, and similar disorders. Similarly, undiagnosed atrial fibrillation or Bradycardia can lead to rhythm-related co-morbidity conditions. Close patient following is needed to minimize risks of future complications.

Increasing the frequency of clinical follow-up is neither practicable nor necessary in all cases, particularly as over prescribed follow-up can adversely affect quality of life and increase healthcare costs. Moreover, physiometry collected during clinical visits only provide an intermittent "snapshot" of patient wellness removed in both time and place from real world situations that the patient encounters. Conventional patient therapy monitoring systems, however, fail to adequately address providing effective patient following that is closely tied to specific medical therapy regimens.

U.S. Pat. No. 6,168,563, to Brown, discloses a system and method that enables a healthcare provider to monitor and manage a health condition of a patient. A clearinghouse computer communicates with the patient through a data management unit, which interactively monitors the patient's health condition. In a further embodiment, a simple and inexpensive system uses a Nintendo Gameboy to query and allow a patient to enter information and blood glucose measurements. The data is stored in a cartridge that can be accessed directly or via a remote computer. Physiological monitoring devices, such as a blood glucose monitor or peak-flow meter, may also supply patient information. Healthcare professionals can access the patient information through the clearinghouse computer, which can process, analyze, print, and display the data. Although the clearinghouse computer can generate scripts of patient queries to address specific healthcare concerns identified by a physician, Brown fails to disclose corroborating monitoring results to a medical therapy regimen.

U.S. Pat. No. 6,418,346 issued Jul. 9, 2002, to Nelson et al., describes an apparatus and method for remote therapy and diagnosis that includes a personal data manager (PDM) used in a Web-based network. The PDM cooperates with a programmer to remotely monitor IMDs on a chronic basis. The PDM is implemented to store and forward information to personal computers and similar equipment, or to uplink data from a programmer to a Web-based export data center. The PDM provides an extension to the programmer and operates as a data messenger between the programmer, export data center, and IMDs. Nelson fails to disclose corroborating monitoring results to a medical therapy regimen.

U.S. Pat. No. 6,263,245 issued Jul. 17, 2001, to Snell, describes a system and method for portable implantable device interrogation that can conduct wireless interrogation of an IMD. A portable interrogation device can be directly interfaced with a data processing device, such as a programmer/analyzer. The portable interrogation device includes a control circuit for controlling transmission using telemetry, transmitter for sending signals, receiver for receiving data transmitted by an IMD in response to interrogation signals, memory for storing data received, and electronic communications interface for high-speed delivery of data to the data processing device. However, the device only facilitates relay of data without analysis or processing and fails to provide corroborating monitoring results to a medical therapy regimen.

Therefore, there is a need for providing a patient therapy compliance monitor coupled to actively and regularly monitoring a therapy regimen performed by a patient having a cardiovascular disorder.

SUMMARY OF THE INVENTION

A system and method includes managing a patient diagnosed with a cardiovascular disorder through closely followed remote monitoring. A patient is diagnosed and classified into a clinical stage of disease progression and prescribed a cardiac therapy regimen. At about the same time, the patient is provided a wearable therapy compliance monitor that includes one or more physiological sensors and a communications interface. A monitoring server for processing and evaluation periodically collects the therapy compliance monitor measures and records quantitative and qualitative physiological measures and the recorded patient physiometry. If a trend indicating a significant change in patient well being is detected, a notification is generated by the monitoring server and provided to the healthcare personnel and, in a further embodiment, the patient.

One embodiment provides a system and method for providing closely followed cardiac therapy management through automated patient care. A patient under remote care is enrolled in a monitoring program following commencement of a cardiac therapy regimen to be undertaken by the patient. A wearable monitor, including one or more patient physiology sensors and a wireless interface providing enabling bi-directional data exchange, is provided to the patient. Patient physiometry, including quantitative physiological measures, is periodically collected from the wearable monitor over the wireless interface concomitant to performance of the cardiac therapy regimen. The patient physiometry is evaluated to determine a trend indicating an onset, progression, regression, absence of, and status quo of patient health status.

Still other embodiments will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Patient Mortality and Therapeutic Appropriateness

Figure 1:
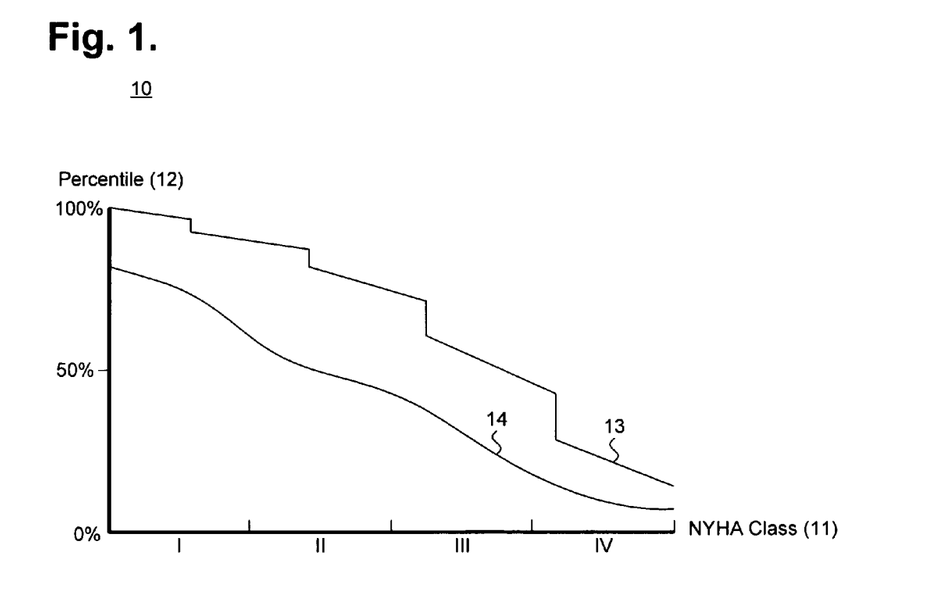
FIG. 1 is a graph showing, by way of example, patient mortality and therapeutic appropriateness as a function of clinical stage.

Patient survivability rate and the suitability of such patients to undertake cardiac therapy are roughly proportionate throughout the progression of a cardiovascular disorder. FIG. 1 is a graph 10 showing, by way of example, patient mortality 13 and therapeutic appropriateness 14 as a function of clinical stage 11. The x-axis 11 represents cardiovascular disease clinical stage, as classified according to New York Heart Association (NYHA) classes. The y-axis 12 represents the percentile of surviving patients and appropriateness of therapy. As the clinical stage 11 of the cardiovascular disorder progresses, patient mortality 13 increases significantly. As a result, the therapeutic appropriateness 14 of such patients undertaking a medical therapy regimen correspondingly decreases as the clinical focus shifts from preventing disease progression to reducing future risk.

A common precipitating cause of cardiovascular disease worsening is inappropriate reduction in the intensity of therapy, such as dietary sodium restriction, reducing physical activity, drug regimen, or in combination of factors, resulting in decompensation in a previously compensated patient. However, close patient following can help prevent or ameliorate further patient decompensation by regularly and continuously monitoring therapy regimen compliance.

Functionality Performance Range

Figure 2:
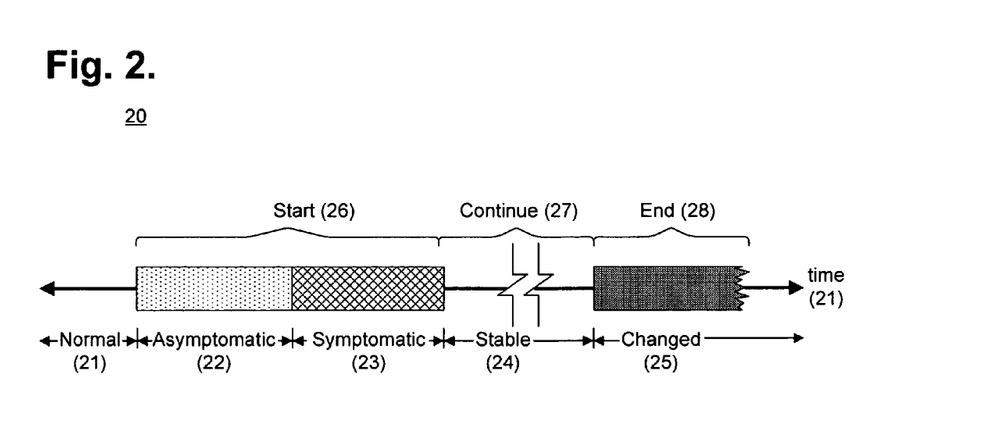
FIG. 2 is a timeline showing clinical stages for providing closely followed cardiac therapy management.

A cardiac therapy regimen can be prescribed to a patient at any time, but the appropriateness of a therapy undertaking is tied closely to the clinical stage of the underlying cardiovascular disorder. FIG. 2 is a timeline 20 showing clinical stages for providing closely-followed cardiac therapy management, in accordance with one embodiment. The x-axis 21 represents time over which the clinical stages of a chronic cardiovascular disorder proceeds.

Patients that present as asymptomatic 22 or symptomatic 23 are generally prescribed a cardiac therapy regimen, preferably, concomitant to an initial diagnosis or treatment, subject to whether therapy is appropriate to their clinical condition. Asymptomatic patients fall under NYHA Class I, whereas symptomatic patients fall into any one of NYHA Classes II, III, or IV. A healthcare provider would generally start 26 a patient on a cardiac therapy regimen that would continue 27 while the patient remained in a stable 24 clinical stage. The regimen would end 28 when the patient presents with a significantly changed prognosis, although the medical therapy regimen may be continued or modified to reestablish a stable condition.

Automated Patient Management Environment

Figure 3:
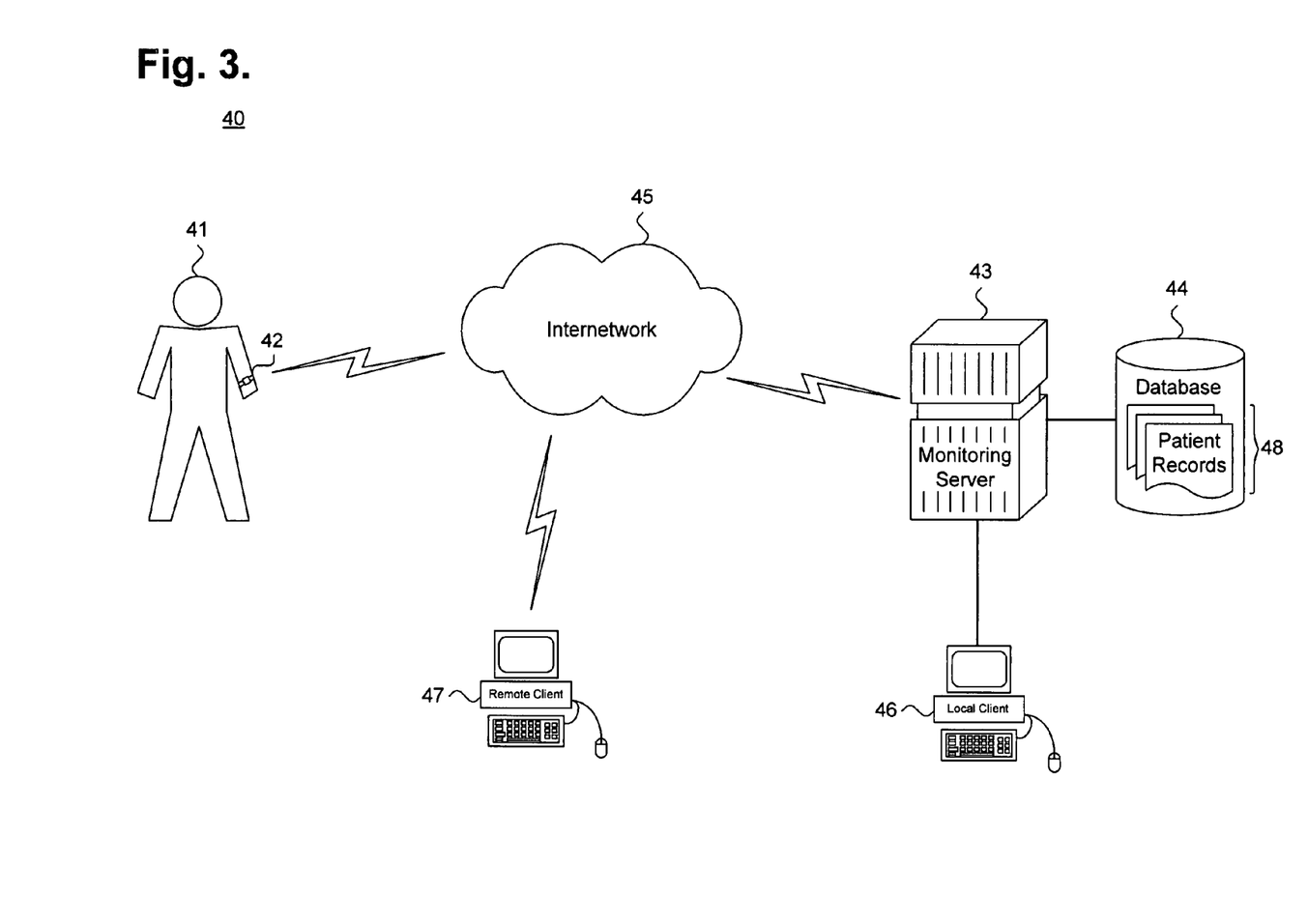
FIG. 3 is a functional block diagram showing, by way of example, closely followed cardiac therapy management in an automated patient management environment.

Cardiac therapy can be closely managed through remote patient care with a wearable therapy compliance monitor and regular monitoring through a centralized monitoring server. FIG. 3 is a functional block diagram showing, by way of example, closely followed cardiac therapy management in an automated patient management environment 40. Automated patient management encompasses a range of activities, including remote patient management and automatic diagnosis of patient health, such as described in commonly assigned U.S. Patent application Pub. No. US2004/0103001, published May 27, 2004, pending, the disclosure of which is incorporated by reference. Such activities can be performed proximal to a patient, such as in the patient's home or office, centrally through a centralized server, such from a hospital, clinic or physician's office, or through a remote workstation, such as a secure wireless mobile computing device.

A patient 41 receives a therapy compliance monitor 42, preferably in a wearable form factor, that senses and records patient data, including patient physiology, such as further described below with reference to FIGS. 8 and 9. Patient data includes physiological measures, which can be quantitative or qualitative, parametric data regarding the status and operational characteristics of the IMD, and environmental parameters, such as the temperature and time of day. Other types of patient data are possible. The therapy compliance monitor 42 periodically, or as required, interfaces remotely to a monitoring server 43 over an internetwork 45 to allow the monitoring server 43 to collect the recorded patient physiology for storage and analysis, such as further described below with reference to FIG. 7. In one embodiment, the internetwork 45 is based on the Transmission Control Protocol/Internet Protocol (TCP/IP) network communications specification, although other types or combinations of networking implementations are possible.

The therapy compliance monitor 42 is a form of external medical sensor that can directly measure and record quantitative physiological measures, such as heart rate; heart rate variability and derivatives, such as minimum, maximum, and mean; and physical activity. The therapy compliance monitor 42 can include one or more external sensors and, in a further embodiment, incorporate one or more internal sensors. In addition, the therapy compliance monitor 42 can record qualitative physiological measures through a user interface, such as medical therapy compliance and quality of life indications. Other types of quantitative and qualitative physiological measures are possible. The patient physiometry can be measured on both a continuous or intermittent basis, which, when provided to the monitoring server 43, can be stored in a database 44 in individual patient records 48, such as further described below with reference to FIG. 6.

To ensure patient privacy, the therapy compliance monitor 42 maintains uniquely assigned stored credentials that are exchanged prior to server data transfer, thereby ensuring a secure and legitimate interface. The therapy compliance monitor 42 interfaces directly over the internetwork 45 either through direct means, such as wired connectivity, or preferably through indirect means, such as wireless communications based on, for example, "strong" Bluetooth, IEEE 802.11 wireless fidelity "WiFi" and "WiMax" interfacing standards. The therapy compliance monitor 42 can also interface through cellular communications using, for example, CDMA, GSM, GPRS, and WCDMA, compliant protocols, such as described in commonly-assigned U.S. patent application Ser. No. 10/859,649, filed Jun. 3, 2004, pending, the disclosure of which is incorporated by reference. Other forms of wired and wireless interfacing are possible.

In addition, other devices that serve as sources of patient data that collect and forward patient data either as a primary or supplemental function are possible. Additional patient data source devices include, by way of example, medical therapy devices that deliver or provide therapy to the patient, medical sensors that sense physiological data in relation to the patient, and measurement devices that measure environmental parameters occurring independent of the patient. Each patient data source can generate one or more types of patient data and can incorporate one or more components for delivering therapy, sensing physiological data, measuring environmental parameters, or a combination of functionality.

In a further embodiment, a patient can enter data values directly into a patient data source. For example, answers to health questions could be input into a personal computer or other device that includes interactive user interfacing means, such as a keyboard, display, microphone, and speaker. Such patient-provided data values could also be collected as patient information. Additionally, measurement devices are frequently incorporated into medical therapy devices and medical sensors. Medical therapy devices include implantable medical devices (IMDs), such as pacemakers, implantable cardiac defibrillators (ICDs), cardiac resynchronizers, drug pumps, and neuro-stimulators, and external medical devices (EMDs), such as automatic external defibrillators (AEDs). Medical sensors include implantable sensors, such as implantable heart and respiratory monitors and implantable diagnostic multi-sensor non-therapeutic devices, and external sensors, such as Holter monitors, weight scales, and blood pressure cuffs. Other types of medical therapy, medical sensing, and measuring devices, both implantable and external, are possible.

In a further embodiment, collected patient data can be accessed and analyzed by one or more clients, either locally configured 46 or remotely-interconnected 47. The clients can be used, for example, by clinicians to securely access stored patient data assembled in the database 44 or other repository and to select and prioritize patients for health care provisioning, such as respectively described in commonly-assigned U.S. patent application Ser. No. 11/121,593, filed May 3, 2005, pending, and U.S. patent application Ser. No. 11/121, 594, filed May 3, 2005, pending, the disclosures of which are incorporated by reference. Although described herein with reference to physicians or clinicians, the entire discussion applies equally to organizations, including hospitals, clinics, and laboratories, and other individuals or interests, such as researchers, scientists, universities, and governmental agencies, seeking access to the patient data.

The collected patient data can also be evaluated for the occurrence of one or more conditions, such as described in related, commonly-owned U.S. Pat. No. 6,336,903, to Bardy, issued Jan. 8, 2002; U.S. Pat. No. 6,368,284, to Bardy, issued Apr. 9, 2002; U.S. Pat. No. 6,398,728, to Bardy, issued Jun. 2, 2002; U.S. Pat. No. 6,411,840, to Bardy, issued Jun. 25, 2002; and U.S. Pat. No. 6,440,066, to Bardy, issued Aug. 27, 2002, the disclosures of which are incorporated by reference.

In a still further embodiment, patient data is safeguarded against unauthorized disclosure to third parties, including during collection, assembly, evaluation, transmission, and storage, to protect patient privacy and comply with recently enacted medical information privacy laws, such as the Health Insurance Portability and Accountability Act (HIPAA) and the European Privacy Directive. At a minimum, patient health information that identifies a particular individual with health- and medical-related information is treated as protectable, although other types of sensitive information in addition to or in lieu of specific patient health information could also be protectable.

Preferably, the monitoring server 43 is a server-grade computing platform configured as a uni-, multi- or distributed processing system, and the clients are general-purpose computing workstations, such as a personal desktop or notebook computer. In addition, the clients 46, 47 are programmable computing devices that respectively execute software programs and include components conventionally found in computing device, such as, for example, a central processing unit (CPU), memory, network interface, persistent storage, and various components for interconnecting these components.

Process Flow

Figure 4:
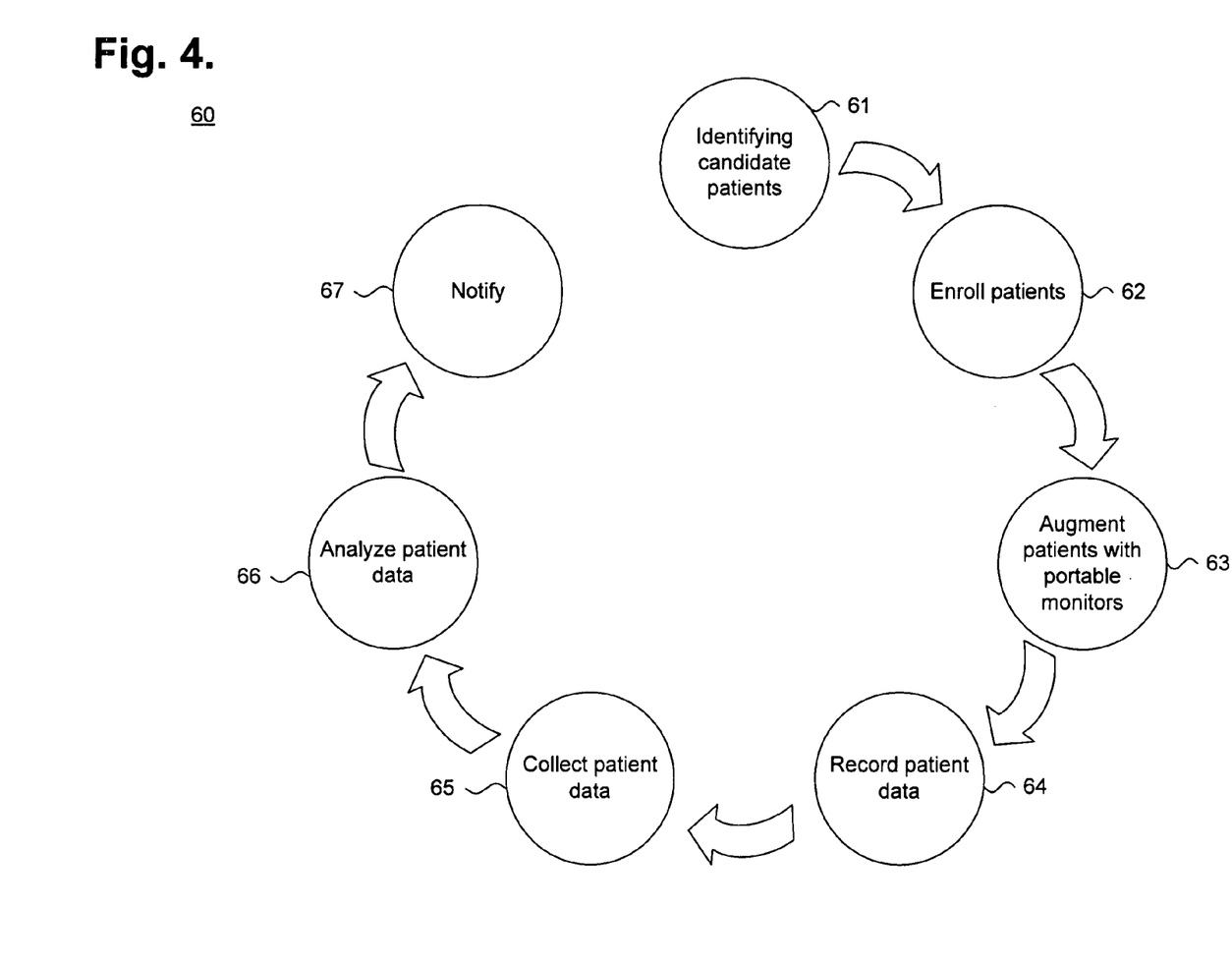
FIG. 4 is a process flow diagram showing providing closely followed cardiac therapy management through automated patient care, in accordance with one embodiment.

Patients are closely-followed by detecting and classifying changes in well-being subsequent to cardiovascular treatments, such as coronary artery bypass grafting or percutaneous coronary artery stenting, using a combination of a wearable therapy compliance monitor and a centralized network information storage and analysis system. FIG. 4 is a process flow diagram showing providing closely followed cardiac therapy management 60 through automated patient care, in accordance with one embodiment. The cardiac therapy management 60 is started at about the same time that a patient begins to undertake a cardiac therapy regimen. Management continues until, and if, significant changes in well being are identified.

A plurality of patients prescribed to perform a cardiac therapy regimen is evaluated to identify patient candidates (operation 61). Patients that have both a remotely monitorable therapy regimen and sufficient access to a network for communicating with a monitoring server are selected and enrolled (operation 62). Each enrolled patient is augmented with a therapy compliance monitor (operation 63), which records physiometry measures as patient data (operation 64) throughout the time period that the cardiac therapy regimen is performed. Periodically, or on-demand, the recorded patient data is collected (operation 65) by a monitoring server for storage into a database and analyzed (operation 66) to determine a presence of any trend indicating an onset, progression, regression, absence, or status quo of patient health status since the most recent, or an earlier, data collection occurred. The analysis of the patient data can include performing statistical analysis, value reduction and derivation, data extrapolation, and threshold evaluation.

In a further embodiment, an initial set of physiological measures collected during an initial time period are grouped into a reference baseline, which is stored into the database to indicate an initial patient health status. The reference baseline can subsequently be used during processing as a point of reference for evaluating patient well being. In a still further embodiment, quality of life physiometry, which includes qualitative physiological measures, can be collected from the wearable monitor over the wireless interface concomitant to performance of the cardiac therapy regimen. The quality of life physiometry can also be used during process as part of determining the patient health status. Other forms of patient data processing are possible. If a predefined alert condition is encountered, a clinician can be notified (operation 67) and, in a further embodiment, appropriate action taken, such as sending a notification in real time or per a schedule or requesting the patient to present to an emergency room or schedule a clinic appointment.

Data Flow

Figure 5:
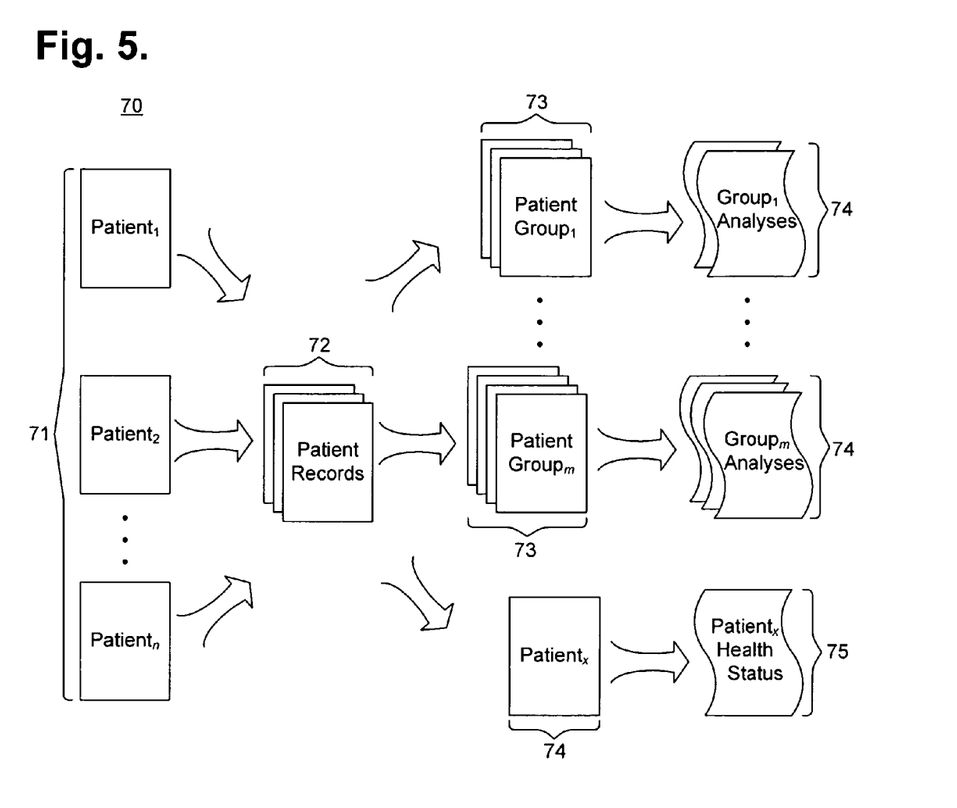
FIG. 5 is a data flow diagram showing patient data collection and evaluation in the environment of FIG. 4.

The patient data available for evaluation grows with each successive phase of cardiac therapy management 60. FIG. 5 is a data flow diagram showing patient data collection and evaluation 70 in the environment 40 of FIG. 4. Individual sets of patient physiometry 71, which each can include quantitative and qualitative physiological measures, are recorded by individual patient compliance monitors.

Periodically, or as required, the sets of patient physiometry 71 are collected by a monitoring server and stored into a database as patient records 72. The patient physiometry 71 can either be requested or "polled" from each therapy compliance monitor by the monitoring server or unilaterally sent or "pushed" to the monitoring server by each therapy compliance monitor. Once available in the database, the patient data can be categorized by patient group 73 based on, for instance, common traits, such as pretreatment phenotype, treatment medication, therapeutic response, and similar factors, or into individualized patient histories 74. The patient groups can be evaluated to generate group analyses 74 to provide an integrated contextual view of patient population health status and other studies. Similarly, each patient history 74 can be evaluated to generate a patient health status 75. Other types of evaluation and analyses of patient populations, groups, and individuals are possible.

Data Structure

Figure 6:
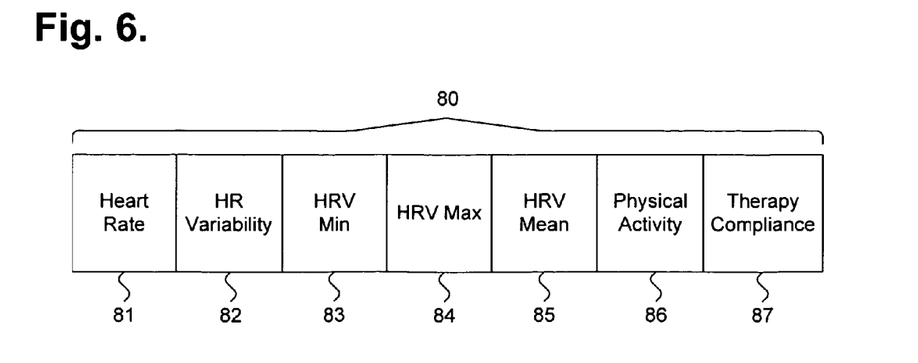
FIG. 6 is a data structure diagram showing, by way of example, patient data collectable by a therapy compliance monitor operating in the environment of FIG. 4.

The type and amount of patient data collected by a therapy compliance monitor is constrained by the available physiology sensors and resources available for tracking and recording physiological measures, in particular, memory for transient storage of recorded physiological measures, pending collection by a monitoring server. FIG. 6 is a data structure diagram showing, by way of example, patient data 80 collectable by a therapy compliance monitor operating in the environment 40 of FIG. 4. In one embodiment, the patient data 80 includes both quantitative and qualitative physiological measures. The quantitative measures include heart rate 81 and heart rate variability 82, as well as measures derivative from heart rate variability, such as minimum 83, maximum 84, and mean 85. In addition, an activity sensor tracks the relative movement and activity level of the patient to gauge physical activity 86. Qualitative physiological measures include therapy compliance 87 as subjectively quantified by the patient. For example, medication compliance can be expressed as full, partial, or negative, which respectively reflect strict or partial adherence to taking prescribed medications and non-compliance. Other types and forms of quantitative and qualitative physiological measures are possible.

Monitoring Server

Figure 7:
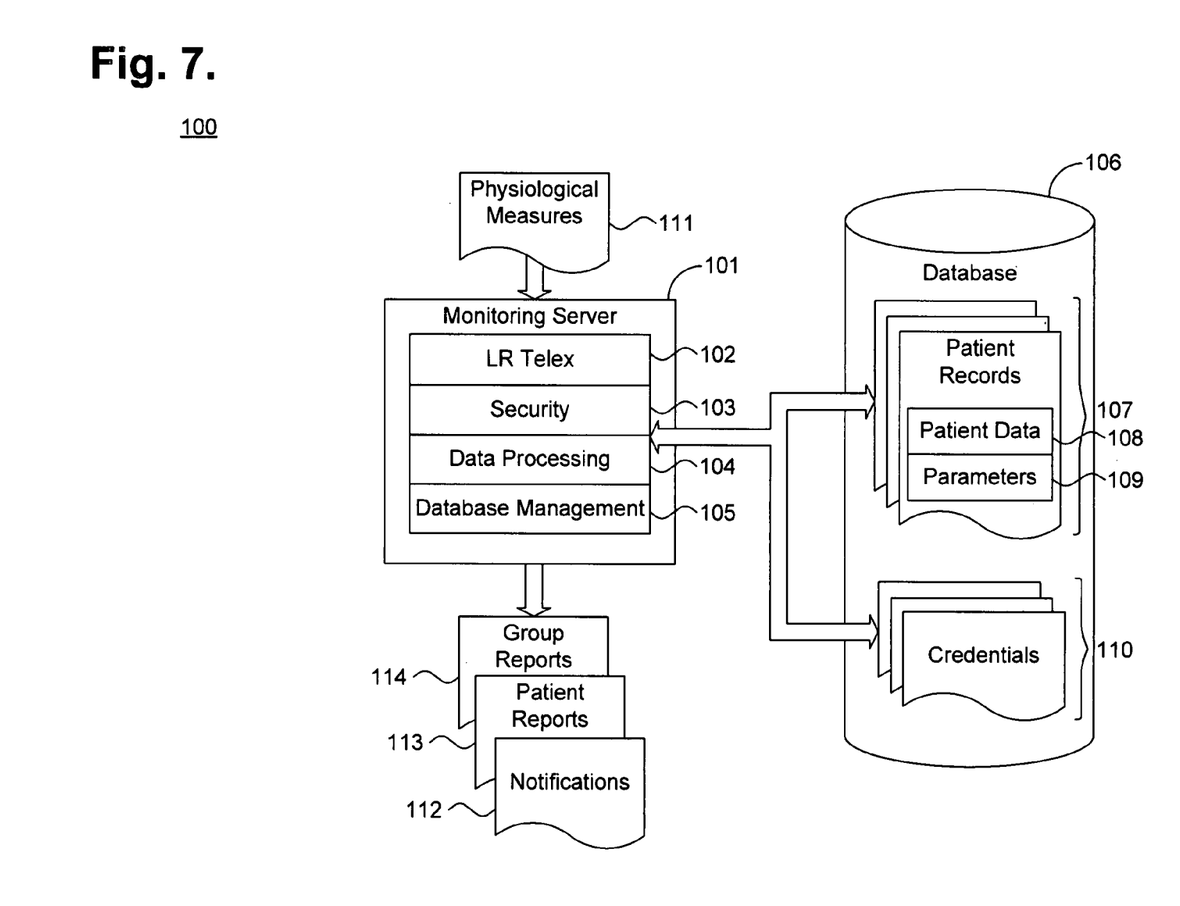
FIG. 7 is a functional block diagram showing a monitoring server for use in the environment of FIG. 4.

The monitoring server regularly or periodically collects patient data recorded by individual therapy compliance monitors and determines whether each patient is in compliance with their respective prescribed cardiac therapy regimen. FIG. 7 is a functional block diagram 100 showing a monitoring server 101 for use in the environment 40 of FIG. 4. The monitoring server 101 executes a sequence of programmed process steps, such as described above with reference to FIG. 4, implemented, for instance, on a programmed digital computer platform.

A monitoring server 101 is operatively coupled to a database 106 in which patient records 107 and credentials 110 are maintained and stored. The patient records 107 store patient data 108 collected as physiological measures 110 by the individual therapy compliance monitors and parameters 109 that define the types and frequencies of patient data collected. The credentials 110 are used to authenticate each therapy compliance monitor to ensure patient privacy. Other types of data can be stored in the database 106.

The monitoring server 101 includes modules for long-range telemetry ("LR Telex") 102, security 103, data processing 104, and database management 105. Long range telemetry 102 implements a telemetric interface for communicating with therapy compliance monitors and includes wired or wireless interfaces, such as "WiFi," "WiMax," and "strong" Bluetooth. Other types of long-range telemetry are possible. Security 103 handles authentication through use of the stored credentials 110 and provides primary and secondary security, such as encryption, decryption, certification, compression, and decompression, in concert with the exchange of patient data. Data processing 104 performs a core set of functions to evaluate and analyze the collected patient data to ensure compliance and generates notifications 112 when substantial changes in a patient's well being might dictate changes in the therapy regimen. Notifications can be sent in real time or per a schedule. Data processing 104 also includes generating patient reports 113 and group reports 114 that respectively include patient and group analyses. Finally, database management 105 maintains the patient records 107 and credentials 110 in the database 106 as structured data. Other server operations and functionality are possible.

Therapy Compliance Monitor

Each therapy compliance monitor serves as an immediate source of patient data recorded during the undertaking of the cardiac therapy regimen by the patient. Notifications to the patient can also be sent via a therapy compliance monitor, either in real time or per a schedule. FIG. 8 is a functional block diagram 120 showing a therapy compliance monitor 121 in wearable form factor for use in the environment 40 of FIG. 4. A wearable form factor enables the device repeater 121 to be worn by the patient and can be implemented as either a stand-alone device or integrated into a microprocessor-equipped device, such as a watch. Other types of wearable form factors are possible.

Preferably, the monitor 121 can be manufactured at low cost and can be made available to patients for use in-clinic and at large. The relative affordability and availability of the monitor 121 makes therapy compliance monitoring more accessible and timely than current methods available using, for instance, a conventional programmer, due to the user-friendly user interface and the ability to track and follow patient physiometry on a regular and continuous basis throughout a cardiac therapy regimen.

The therapy compliance monitor 121 includes a user interface 122 that includes a display 122 for graphically displaying physiological indications 127 and information 128, such as date and time, a plurality of patient-operable controls 123, a speaker 124, and a microphone 125 for providing an interactive user interface. The device 121 is preferably interfaced to the monitoring server through either RF telemetry, cellular telephone connectivity or other forms of wireless communications, as facilitated by antenna 126. The display 122 and speaker 124 provide visual and audio indicators while the controls 123 and microphone 125 enable patient feedback. In addition, one or more external sensors (not shown) can be interfaced or, in a further embodiment, integrated into the device 121 for directly monitoring patient health information.

The types of indications 127 that can be provided to the patient non-exclusively include:
(1) Health measurements
(2) Data transmission in-process indication
(3) Alert condition detection
(4) Memory usage
(5) Battery charge The device 121 can also include a physical interface 129 that allows the device to be physically connected or "docked" to an external data processing device for high-speed non-wireless data exchange.

Figure 8:
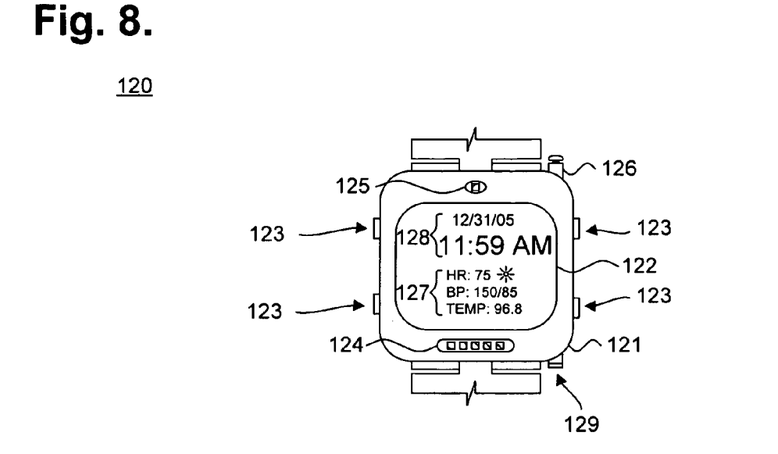
FIG. 8 is a functional block diagram showing a therapy compliance monitor in wearable form factor for use in the environment of FIG. 4.
Figure 9:
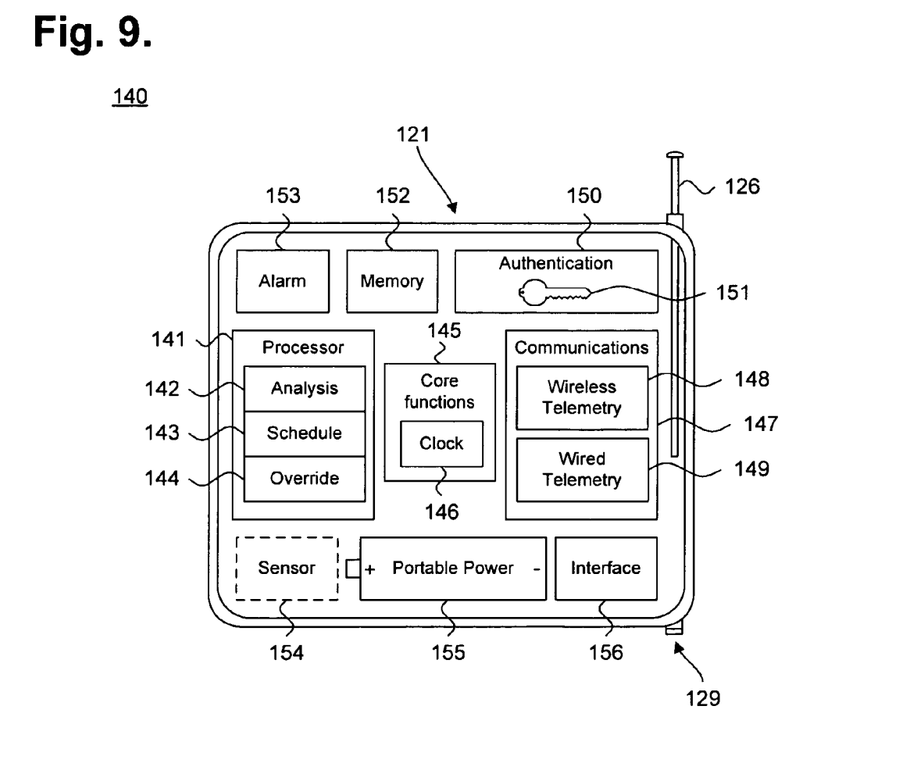
FIG. 9 is a functional block diagram showing, by way of example, the internal components of the therapy compliance monitor in the wearable form factor of FIG. 8.

FIG. 9 is a functional block diagram 140 showing, by way of example, the internal components of the therapy compliance monitor 121 in the wearable form factor of FIG. 8. By way of example, the device 121 includes a processor 140, memory 152, authentication module 150, communications module 147, physical interface 156, one or more optional integrated sensors 154, and alarm 153. Each of the components is powered by a power supply 155, such as a rechargeable or replaceable battery. The internal components are provided in a housing with provision for the antenna 126 and physical interface 129. The device 121 receives physiological data readings from one or more external sensors (not shown) and, if provided, internal sensors.

The processor 141 enables the therapy compliance device to control the authentication and secure transfer of both non-sensitive and sensitive information between the sensors and the monitoring server 125. The processor 141 also provides functionality embodied in an analysis module 142, schedule module 143, and override module 144. The analysis module 142 controls the translation, interpretation and display of patient health information. The schedule module 143 controls the periodic interfacing of the device 121 to the monitoring server. The override module 144 controls patient-initiated interrogation. Other control modules are possible.

The communications module 147 includes a wireless telemetry module 148 and a wired telemetry module 149 for interfacing to the monitoring server. The therapy compliance monitor 121 interfaces to the monitoring server preferably through RF telemetry or via cellular network or other form of wireless interface. The authentication module 150 is used to securely authenticate and encrypt and decrypt sensitive information using a retrieved cryptographic key 151. The memory 152 includes a memory store, in which recorded physiological measures are transiently stored pending collection by the monitoring server. The physical interface 156 controls the direct physical connecting of the device 121 to an external device or supplemental accessory, such as a recharging "dock" or other similar device. The optional integrated sensor 154 directly monitors patient health information, such as patient activity level. Lastly, the alarm 153 provides physical feedback to the patient, such as through a visual, tactual or audible warning, for example, a displayed message or flashing light, vibration, or alarm tone, respectively. Other internal components are possible, including removable memory components.

While the invention has been particularly shown and described as referenced to the embodiments thereof, those skilled in the art will understand that the foregoing and other changes in form and detail may be made therein without departing from the spirit and scope of the invention.

What is claimed is:

1. An method for providing closely-followed cardiac therapy management through automated patient care, comprising:
    selecting a patient having both a remotely monitorable therapy regimen and sufficient access to a network for communicating with a monitoring server;
    enrolling the patient under remote care in a monitoring program following commencement of a cardiac therapy regimen to be undertaken by the patient;
    providing a wearable monitor comprising one or more patient physiology sensors and a wireless interface providing enabling bi-directional data exchange;
    periodically collecting patient physiometry comprising quantitative physiological measures from the wearable monitor over the wireless interface concomitant to performance of the cardiac therapy regimen;
    evaluating the patient physiometry to determine a trend indicating an onset, progression, regression, absence of, and status quo of a patient health status;
    forming one or more patient groups that each comprise sets of the qualitative physiological measures for a plurality of patients; and
    analyzing the qualitative physiological measures sets in the patient groups based on one or more of pre-treatment phenotype, therapeutic response, and medication administered.

2. A method according to claim 1, further comprising:
    comparing the trend to predefined alert conditions; and
    generating a notification if at least one predefined alert condition is met.

3. A method according to claim 1, further comprising: performing processing of the patient physiology comprising at least one of 3 statistical analysis, value reduction and derivation, data extrapolation, and threshold evaluation.

4. A method according to claim 1, further comprising: grouping the patient physiology collected during an initial time period into an initial physiological measures set; and processing the initial physiological measures set in a reference baseline indicating an initial patient health status.

5. A method according to claim 1, further comprising:
    collecting quality of life physiometry comprising qualitative physiological measures from the wearable monitor over the wireless interface concomitant to performance of the cardiac therapy regimen; and
    evaluating the quality of life physiometry as part of determining the patient health status.

6. A method according to claim 1, wherein the quantitative physiological measures are collected by the wearable monitor on at least one of a continuous and intermittent basis.

7. A method according to claim 1, wherein the physiological measures are selected from the group comprising heart rate, heart rate variability, heart rate variability minimum, heart rate variability maximum, heart rate variability mean, physical activity, and medical therapy compliance.

8. A method according to claim 1, wherein the cardiac therapy regimen is selected from the group comprising medication, dietary restriction or modification, and physical activity restriction.

9. A non-transitory computer-readable storage medium holding code for performing the method according to claim 1.

10. An apparatus for providing closely-followed cardiac therapy management through automated patient care, comprising:

means for selecting a patient having both a remotely monitorable therapy regimen and sufficient access to a network for communicating with a monitoring server;

means for enrolling the patient under remote care in a monitoring program following commencement of a cardiac therapy regimen to be undertaken by the patient;

means for monitoring a patient with a wearable device, wherein the wearable device comprises one or more patient physiology sensors and a wireless interface providing enabling bi-directional data exchange;

means for periodically collecting patient physiometry comprising quantitative physiological measures from the wearable monitor over the wireless interface concomitant to performance of the cardiac therapy regimen;

means for evaluating the patient physiometry to determine a trend indicating an onset, progression, regression, absence of, and status quo of a patient health status;

means for forming one or more patient groups that each comprise sets of the qualitative physiological measures for a plurality of patients; and     means for analyzing the qualitative physiological measures sets in the patient groups based on one or more of pre-treatment phenotype, therapeutic response, and medication administered.

* * * * *